(12) United States Patent
Lee et al.

(10) Patent No.: US 9,717,416 B2
(45) Date of Patent: Aug. 1, 2017

(54) OPTICAL ZOOM PROBE

(71) Applicant: Samsung Electronics Co., Ltd., Suwon-si (KR)

(72) Inventors: Seung-wan Lee, Suwon-si (KR); Eun-sung Lee, Hwaseong-si (KR); Jong-hyeon Chang, Suwon-si (KR); Kyu-dong Jung, Suwon-si (KR); Min-seog Choi, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 608 days.

(21) Appl. No.: 14/105,282

(22) Filed: Dec. 13, 2013

(65) Prior Publication Data
US 2014/0194750 A1    Jul. 10, 2014

(30) Foreign Application Priority Data
Jan. 4, 2013    (KR) .................... 10-2013-0000976

(51) Int. Cl.
*A61B 5/00*    (2006.01)

(52) U.S. Cl.
CPC .................. *A61B 5/0064* (2013.01)

(58) Field of Classification Search
None
See application file for complete search history.

(56) References Cited

U.S. PATENT DOCUMENTS

| | | | |
|---|---|---|---|
| 7,072,045 B2 | 7/2006 | Chen et al. | |
| 7,310,150 B2 | 12/2007 | Guillermo et al. | |
| 7,884,922 B2 | 2/2011 | Brotsack | |
| 2004/0201846 A1* | 10/2004 | Mullani | A61B 5/0059 356/369 |
| 2007/0139657 A1* | 6/2007 | Ishimaru | G01B 11/2441 356/511 |
| 2008/0013066 A1* | 1/2008 | Brotsack | G03F 7/70108 355/71 |
| 2009/0021823 A1* | 1/2009 | Heim | G02B 3/14 359/290 |
| 2009/0072037 A1* | 3/2009 | Good | G02B 3/14 235/462.35 |
| 2014/0092388 A1 | 4/2014 | Lee et al. | |

FOREIGN PATENT DOCUMENTS

| FR | EP 1798958 A1 * | 6/2007 | .............. G02B 5/005 |
|---|---|---|---|
| KR | 10-2014-0042464 A | 4/2014 | |

* cited by examiner

*Primary Examiner* — Joseph M Santos Rodriguez
(74) *Attorney, Agent, or Firm* — Sughrue Mion, PLLC

(57) ABSTRACT

Exemplary embodiments disclose an optical zoom probe including an aperture adjuster configured to adjust an aperture in which light transmitted by a light transmitter passes, a focus adjuster configured to focus the light passed through the aperture and adjust a focal length to an ultra-close location and a close location, and a filter which includes a center region in which incident light passes without change, and a filter region which surrounds the center region and increases a depth of focus (DOF) of light that is focused on the ultra-close location.

19 Claims, 12 Drawing Sheets

OPTICAL ZOOM PROBE

CROSS-REFERENCE TO RELATED APPLICATION

This application claims priority from Korean Patent Application No. 10-2013-0000976, filed on Jan. 4, 2013, in the Korean Intellectual Property Office, the disclosure of which is incorporated herein in its entirety by reference.

BACKGROUND

1. Field

Exemplary embodiments relate to optical zoom probes. In particular, exemplary embodiments relate, to an optical zoom probe which is capable of performing a close distance scan and an ultra-close distance scan.

2. Description of the Related Art

In the field of medical imaging, there are increasing demands for information about the surface of tissue (e.g., a human body or a skin), and technology for precisely taking a photograph of a plane section of a body part under the skin. In particular, since most cancers are generated under epithelial cells and propagated into hypodermal cells where blood vessels are present, damage may be drastically reduced if the cancers are detected early. In existing imaging technology, such as magnetic resonance imaging (MRI), x-ray computed tomography (CT), and an ultrasound, an internal plane section of a body part under the skin may be photographed. However, the image obtained from the plane section during photography has a low resolution, making it impossible to detect small sizes of early cancers. Further, in contrast with existing imaging technology, optical coherence tomography (OCT) in the related art uses light in contrast with existing imaging technology. Thus, a depth to which light penetrates a body part under the skin is only about 2~3 mm. However, an image obtained using light has a resolution about ten times as high as the resolution of an image obtained using ultrasonic waves. Thus, recent OCT in the related art is useful in the diagnosis of early cancers, at approximately 50 to 100 μm. However, since OCT in the related art still provides low resolution, in comparison with microscopes, OCT fails to replace a biopsy and a histology, which are still used in determining cancers.

Instead of performing a biopsy, some OCT researchers in the related art have recently conducted research into real-time diagnosis of cancers inside tissue by combining the tomography characteristics of OCT with a high-resolution surface photographing method, such as a confocal microscope. However, an objective lens of a microscope needs an optical system with a high numerical aperture (NA) in order to obtain a high horizontal resolution. Further, OCT in the related art needs an optical system with a low NA, in which a light spot size in a depth direction is relatively uniform, i.e., a depth of focus (DOF) is large, in order to obtain depth information. Moreover, in contrast with an OCT mode, in an optical coherence microscopy (OCM) mode of the related art, a DOF is small in a z-axis direction. Thus, a longer DOF is required.

SUMMARY

Exemplary embodiments may provide optical zoom probes capable of performing a high-resolution scan, while moving a focal point in an ultra-close distance section and a close distance section, and obtaining a longer depth of focus (DOF) in the ultra-close distance section.

Additional aspects will be set forth in part in the description which follows and, in part, will be apparent from the description, or may be learned by practice of the presented embodiments.

According to an aspect of the exemplary embodiments, an optical zoom probe includes an aperture adjuster configured to adjust an aperture in which light transmitted by a light transmitter passes; a focus adjuster configured to focus the light having passed through the aperture and adjust a focal length to an ultra-close location and a close location; and a filter which comprises a center region in which incident light passes without change, and a filter region which surrounds the center region and increases a depth of focus (DOF) of light which is focused on the ultra-close location.

The center region may have a size equal to or greater than a size of an incident light beam which has been reduced by the aperture adjuster in a close mode.

A radius of the center region may be about 0.2 to about 0.5 times a radius of the aperture of the aperture adjuster in an ultra-close mode, and a minimum diameter of the center region may include a diameter of the aperture of the aperture adjuster in a close mode.

A minimum radius of the filter region may be equal to or greater than a radius of the aperture of the aperture adjuster in a close mode.

The filter region may be provided in a ring structure.

The center region may be provided in an opening structure or a transparent flat plate structure.

The filter region may be a cubic filter that satisfies an equation of $\theta(x, y) = \alpha(x^\beta + y^\beta)$, wherein a value of $\alpha$ is approximately 0.0001 to 0.02, and a value of $\beta$ is approximately 2.6 to 3.1.

The filter region may be a cubic-petal filter that satisfies an equation of $\theta(x, y) = \alpha(x^3 + y^3) + \beta(x^2 y + xy^2)$, wherein a value of $\alpha$ is approximately −0.005 to 0.005 and a value of $\beta$ is approximately −0.015 to 0.015.

The filter may be included in the aperture adjuster or may be provided as a phase filter on a traveling path of parallel light beams before and after the aperture adjuster.

The filter may be provided in an aspherical shape or may be a hybrid type on a last lens surface in which parallel light passed through the aperture adjuster is directed.

The optical zoom probe may further include an aspherical lens between the focus adjuster and a target, wherein the aspherical lens has a positive power.

The focus adjuster may include a first liquid lens and a second liquid lens, in which the first liquid lens and the second liquid lens have curvatures which are independently controlled.

In a close scan mode, the first liquid lens and the second liquid lens may be driven to have concave lens surfaces.

In an ultra-close scan mode, at least one of the first liquid lens and the second liquid lens may be driven to have a convex lens surface.

In the ultra-close scan mode, one of the first liquid lens and the second liquid lens which is closer to the target, may be driven to have the convex lens surface.

At least one of the first liquid lens and the second liquid lens may further include a transparent film having a curved surface, and the curved surface of the transparent film may be a lens surface in a close scan mode, and may not be the lens surface in an ultra-close scan mode.

Each of the first liquid lens and the second liquid lens may form a lens surface using a surface of a fluid, and a focal length may be controlled by adjusting a shape of the lens surface according to a movement of the fluid.

The fluid may be moved in opposite directions in the first liquid lens and the second liquid lens.

The fluid movement may occur according to an electrowetting method. At least one of the first liquid lens and the second liquid lens may include a first fluid which is transparent; a second fluid which is transparent, and does not mix with the first fluid; a chamber which includes an internal space to accommodate the first fluid and the second fluid; a first surface which is an interface between the first fluid and the second fluid and forms the lens surface; a second surface which is an interface between the first fluid and the second fluid and induces a change in the curvature of the lens surface; a first intermediate plate which is disposed within the chamber and comprises a first through hole having a diameter corresponding to a diameter of the lens surface and a second through hole which forms a passage for the second fluid; and an electrode unit which forms an electric field and changes a location of the second surface.

The first fluid may be a polar liquid, and the second fluid may be a vapor or a non-polar liquid.

The fluid movement may occur according to a pressure type method.

The optical zoom probe may further include at least one of a first lens and a second lens, wherein the first lens collimates the light transmitted by the light transmitter and transmits collimated light to the aperture adjuster, and the second lens is disposed between the aperture adjuster and the focus adjuster.

The filter may be provided in an aspherical shape or may be formed as a hybrid type on a last lens surface in which parallel light of the second lens is directed.

The aperture adjuster may be a liquid iris in which aperture size is adjusted according to a microelectrofluidic method.

The aperture adjuster may include a chamber which provides a space in which a fluid is moved; a first fluid and a second fluid, which are disposed within the chamber and do not mix with each other, and one of the first fluid and the second fluid is formed of a transparent material and an other one other of the first fluid and the second fluid is formed of a light-blocking or light-absorptive material; and an electrode unit which is disposed on an inner surface of the chamber and is obtained by arranging at least one electrode in which a voltage is applied to form an electric field within the chamber. The aperture, in which light passes, may be adjusted by a change in the location of an interface between the first fluid and the second fluid according to the electrical field within the chamber.

One of the first fluid and the second fluid may be a liquid metal or a polar liquid, and an other one may be a vapor or a non-polar liquid.

The filter may be formed as a phase filter on an output side of the aperture adjuster.

The light transmitter may include an optical fiber.

According to another aspect of the exemplary embodiments, an image diagnosis system includes a light source device; the optical zoom probe which irradiates light transmitted by the light source device on a target to be scanned; and a detector which detects an image of the target from light reflected by the target.

According to another aspect of the exemplary embodiments, an optical zoom probe includes an aperture adjuster configured to adjust an aperture in which light passes through; a focus adjuster configured to focus the light passed through the aperture and adjust a focal length; and a filter configured to increase a depth of focus (DOF) of light which is focused on an ultra-close location, wherein at least one of the aperture adjuster and the focus adjuster is disposed in a slant configuration.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION OF THE EXEMPLARY EMBODIMENTS

Figure 1:
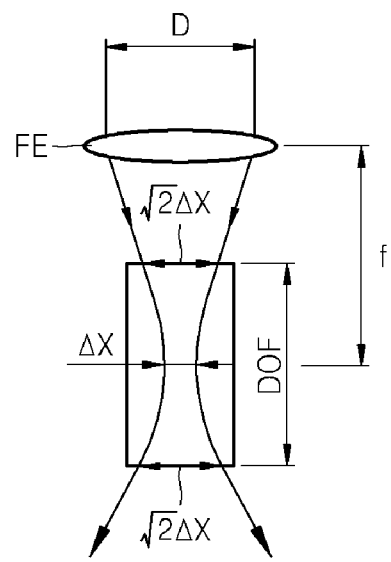
FIG. 1 is a conceptual diagram for explaining a relationship between a horizontal resolution and a depth of focus (DOF)

Reference will now be made in detail to embodiments, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are merely described below, by referring to the figures, to explain aspects of the present description. Expressions such as "at least one of," when preceding a list of elements, modify the entire list of elements and do not modify the individual elements of the list.

Optical zoom probes according to embodiments will now be described in detail with reference to the accompanying drawings. Like reference numerals in the drawings denote like elements, and, in the drawings, the sizes of elements may be exaggerated for clarity and for convenience of explanation.

FIG. 1 is a conceptual diagram for explaining a relationship between a horizontal resolution and a depth of focus (DOF).

A Gaussian beam has a beam waist having a finite size $\Delta x$ instead of a point when being focused, and the finite size $\Delta x$ is determined by an aperture D and a focal length f, using Equation 1 below:

$$\Delta x = \frac{4}{\pi} \lambda \frac{f}{D} \tag{1}$$

The finite size $\Delta x$ is related with a horizontal resolution. In other words, the smaller the finite size $\Delta x$, the higher the horizontal resolution. As expressed in Equation (1), the finite size $\Delta x$ is proportional to f/D, and a numerical aperture (NA) of a focusing lens FE is proportional to D/f. Thus, an optical system having a large NA to decrease the finite size $\Delta x$ is required to obtain a high horizontal resolution.

The DOF is determined in such a range that a beam diameter is $\sqrt{2}\Delta x$, using Equation 2 below:

$$DOF = \frac{\pi}{2\lambda}(\Delta x)^2 \tag{2}$$

The DOF denotes a range in which the size of a beam spot is relatively uniform in a depth direction. In order to obtain image information depending on a depth, e.g., a tomography image of human anatomy, an optical system having a large DOF, i.e., an optical system having a small NA, is needed.

Thus, is a trade-off relationship between the horizontal resolution and the DOF.

An optical zoom probe according to an embodiment may obtain a horizontal resolution and a DOF necessary to scan a target in high resolution at an ultra-close distance or a close distance. The ultra-close distance denotes a case where a distance between the last lens of the optical zoom probe to the surface of a target, e.g., tissue, is about 2 mm or less, and the close distance denotes a case where the distance between the last lens of the optical zoom probe to the surface of the target, e.g., the tissue, is about 30 mm or less.

Figure 2:
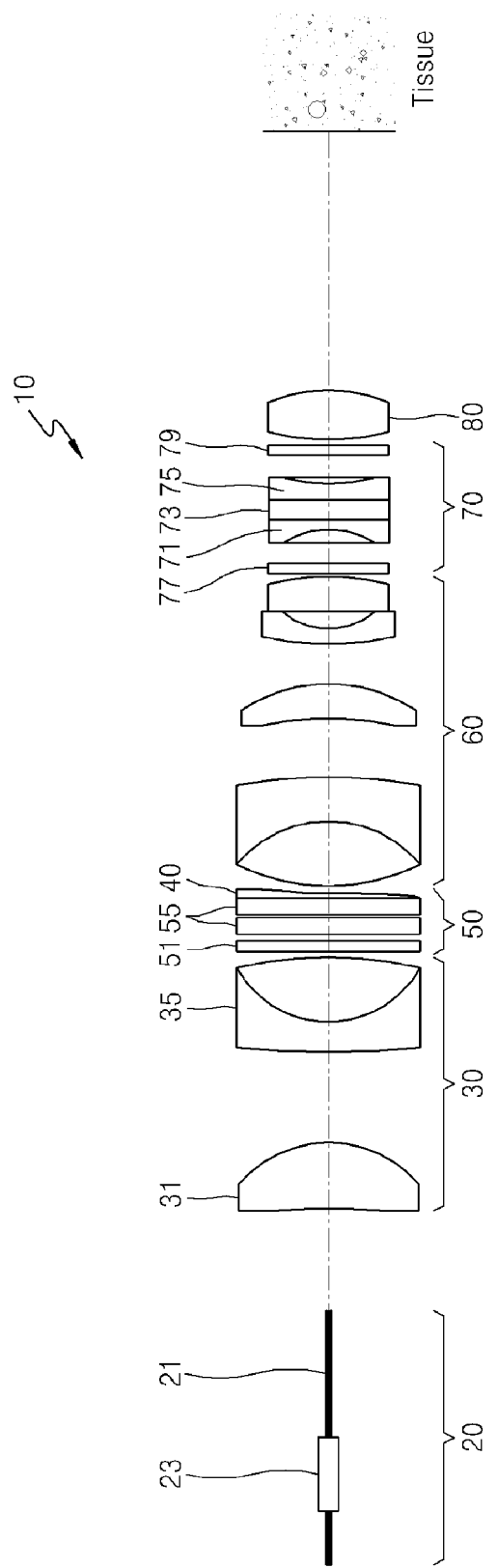
FIG. 2 is a schematic view of an overall optical structure of an optical zoom probe according to an embodiment.

FIG. 2 is a schematic view of an overall optical structure of an optical zoom probe 10 according to an embodiment.

Referring to FIG. 2, the optical zoom probe 10 includes an aperture adjuster 50, which adjusts an aperture through which light transmitted by a light transmission unit 20 passes, a focus adjustment unit 70, which includes first and second liquid lenses 71 and 75 designed such that their curvatures are independently adjusted, and a filter unit 40 provided to increase the DOF of light that is focused on an ultra-close location. The optical zoom probe 10 may further include a lens 80 having positive power to optimize focusing, between the focus adjustment unit 70 and a target, e.g., tissue, which is to be inspected. The lens 80 may be an aspherical lens. The optical zoom probe 10 may further include at least one of a first lens unit 30, which collimates the light transmitted by the light transmission unit 20 and transmits the collimated light to the aperture adjuster 50, and a second lens unit 60 disposed between the aperture adjuster 50 and the focus adjustment unit 70. FIG. 2 and the remaining drawings exemplarily illustrate a case where the optical zoom probe 10 includes both the first lens unit 30 and the second lens unit 60. Although the optical zoom probe 10 is hereinafter described based on an optical system illustrated in FIG. 2, exemplary embodiments are not limited thereto, and various modifications and other equivalent embodiments may be made.

The light transmission unit 20 includes an optical fiber 21, and may further include a scanner 23, which is assembled to an end of the optical fiber 21. The scanner 23 is an actuator which changes a light path by inducing deformation of the optical fiber 21. The scanner 23 may be formed in the shape of, e.g., a piezoelectric actuator or a cantilever that uses a piezoelectric body, a shape-memory alloy, etc. The scanner 23 may also be formed of various other materials using various methods.

In order to remove noise due to reflected light, an end of the optical fiber 21, which is scanned, may have an inclination of about 12 degrees or less, or may be non-reflectively coated, or may be formed to have both of the two features, i.e., an inclination of about 12 degrees or less and non-reflective coating.

The first lens unit 30 collimates the light transmitted by the light transmission unit 20 such that parallel light or substantially parallel light is incident upon the aperture adjuster 50. The first lens unit 30 may include at least one lens. For example, the first lens unit 30 may include a singlet lens 31 and a doublet lens 35, disposed separate from the singlet lens 31. Although the first lens unit 30 includes the singlet lens 31 and the doublet lens 35 in FIG. 2 and the following drawings, this is only an example. Therefore, the lens construction of the first lens unit 30 may vary.

The aperture adjuster 50 adjusts the size of a light beam incident upon the focus adjustment unit 70 in order to change the NA of the focus adjustment unit 70. For example, in an optical coherence microscopy (OCM) mode, which requires a uniform high resolution within a section of about 2 mm in a depth direction of the tissue from an ultra-close distance of about 2 mm or less, the aperture adjuster 50 increases the size of the light beam incident upon the focus adjustment unit 70 in order to obtain a relatively high NA. In an optical coherence tomography (OCT) mode, which requires a uniform spot size within a section of about 2 mm section in the depth direction of the tissue from a close distance of about 2 mm to about 30 mm, the aperture adjuster 50 decreases the size of the light beam incident upon the focus adjustment unit 70 in order to obtain a relatively low NA.

The aperture adjuster 50 may be a liquid iris in which aperture size is adjusted according to microelectrofluidic method. Alternatively, the aperture adjuster 50 may be an iris of which aperture size is mechanically adjusted, or a liquid iris of which aperture size is adjusted using a hydraulic pressure, e.g., using a pump.

Figure 3A:
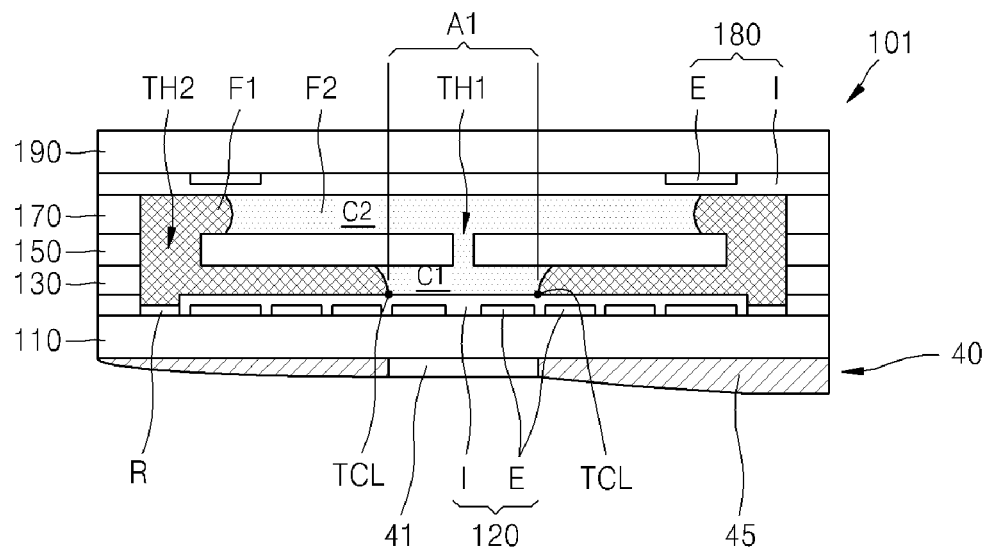
FIGS. 3A and 3B illustrate an example of an aperture adjuster employable in the optical zoom probe of FIG. 2.
Figure 3B:
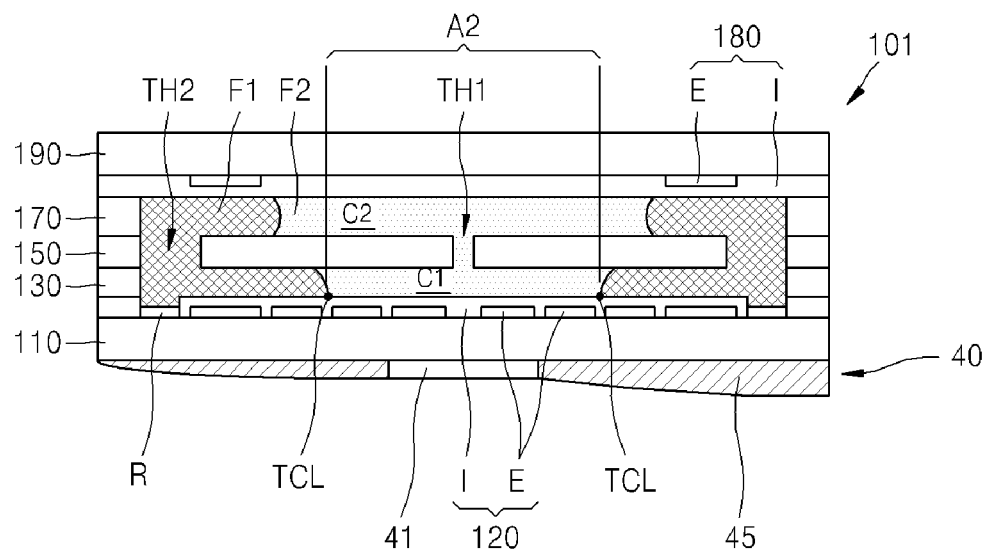
Figure 4:
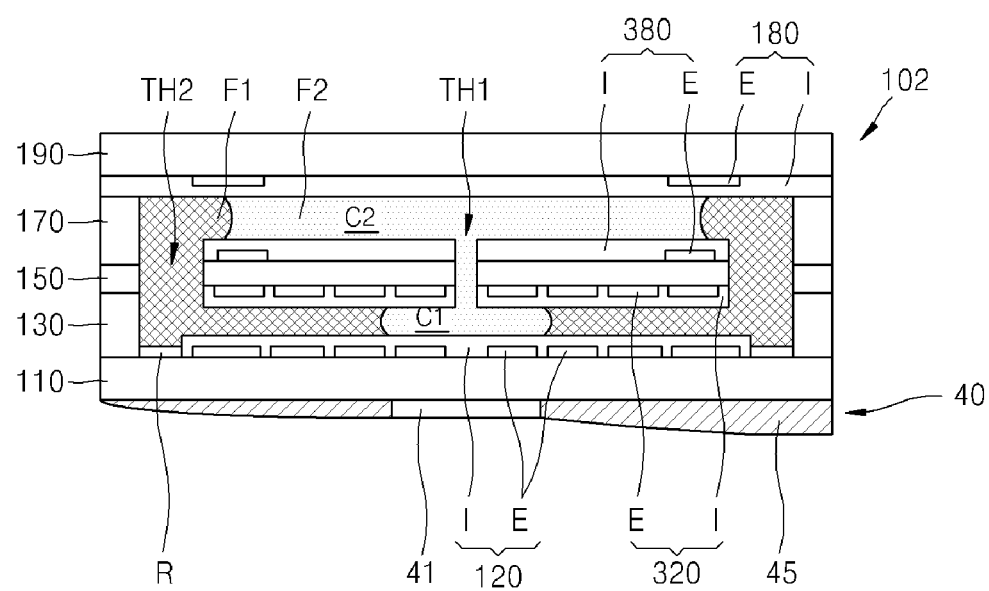
FIG. 4 illustrates another example of an aperture adjuster employable in the optical zoom probe of FIG. 2.

The aperture adjuster 50 may be an aperture adjuster 101 of FIGS. 3A and 3B, or an aperture adjuster 102 of FIG. 4.

FIGS. 3A and 3B illustrate the aperture adjuster 101, which is an example of the aperture adjuster 50 of the optical zoom probe 10 of FIG. 2. FIG. 3A shows an aperture A1 size-adjusted to conform to a close mode, e.g., an OCT mode. FIG. 3B shows an aperture A2 size-adjusted to conform to an ultra-close mode, e.g., an OCM mode.

Referring to FIGS. 3A and 3B, the aperture adjuster 101 may be formed so that a fluid flows according to an electrowetting principle and that an aperture, through which light passes, is size-adjusted into, e.g., the aperture A1 in the OCT mode or the aperture A2 in the OCM mode, depending on the flow of the fluid. The aperture adjuster 101 includes a chamber which forms a space in which a fluid flows, a first fluid F1 and a second fluid F2, which are included in the chamber and do not mix with each other. One of the first fluid F1 and the second fluid F2 is formed of a transparent material, and the other is formed of a light-blocking or light-absorptive material. An electrode unit which is provided on an inner surface of the chamber and is obtained by arranging at least one electrode, to which a voltage is applied, forms an electric field within the chamber. The aperture of the aperture adjuster 101, through which light passes, is adjusted by a change in the location of an interface between the first fluid F1 and the second fluid F2 according to the electric field.

For example, the region of the chamber includes a first channel C1 and a second channel C2 disposed above the first channel C1 such as to be connected to the first channel C1. The range of the aperture may be determined by a change in the location of the interface between the first and second fluids F1 and F2 in each of the first and second channels C1 and C2. The first channel C1 may be defined by a first substrate 110, a second substrate 150 disposed separate from the first substrate 110, and a first spacer 130, which forms an internal space between the first substrate 110 and the second substrate 150. The second substrate 150 has a first through hole TH1 formed on its center and a second through hole TH2 formed on its periphery. The second channel C2 may be defined by the second substrate 150, a third substrate 190 disposed separate from the second substrate 150, and a second spacer 170, which forms an internal space between the second substrate 150 and the third substrate 190.

One of the first and second fluids F1 and F2 may be a liquid metal or a polar liquid, and the other may be a vapor or a non-polar liquid.

The electrode unit may include a first electrode unit 120, which is formed on the first substrate 110 and includes at least one electrode E coated with an insulation material I, and a second electrode unit 180, which is formed on the third substrate 190 and includes at least one electrode E coated with an insulation material I.

The first electrode unit 120 may include a plurality of electrodes in order to digitally control the aperture of the aperture adjuster 101.

The aperture adjuster 101 may further include a ground electrode unit R, which is disposed in at least one place inside the chamber so as to maintain a contact with a polar fluid. For example, the ground electrode unit R may be disposed to maintain a contact with the first fluid F1, which is a polar fluid. To this end, as illustrated in FIGS. 3A and 3B, the ground electrode unit R may be disposed on the first substrate 110, but the location of the ground electrode unit R may be changed.

The electrodes E of the first and second electrode units 120 and 180 may be formed of a transparent conductive material. For example, the electrodes E of the first and second electrode units 120 and 180 may be formed of a metal oxide, such as an indium tin oxide (ITO) or an indium zinc oxide (IZO), a metal nanoparticle dispersion thin film such as gold (Au) or silver (Ag), a carbon nanostructure such as carbon nanotube (CNT) or graphene, or a conductive polymer such as poly(3,4-ethylenedioxythiophene) (PEDOT), polypyrrole (PPy), or poly(3-hexylthiophene) (P3HT).

Since the ground electrode unit R does not need to be transparent because of its location, it may be formed of a metal thin film such as Au, Ag, aluminum (Al), chromium (Cr), or titanium (Ti).

Electrowetting denotes a phenomenon in which the contact angle of an electrolyte droplet on an electrode coated with an insulating material is changed when a voltage is applied to the electrolyte droplet. In other words, the contact angle of the electrolyte droplet varies according to the interfacial tensions of a fluid, the droplet, and the insulating material, at a three-phase contact line (TCL) where the fluid, the droplet, and the insulating material all meet together. When electrowetting is used, the flow of a fluid may be fast and effectively controlled by using a low voltage, and it is possible to reversibly transfer and control the fluid.

When a suitable voltage is applied to one of the electrodes E of the first electrode unit 120, an electromechanical force is exerted on a TCL, e.g., a contact line where the first fluid F1, the second fluid F2, and the insulation material I all meet together, on the actuated electrode E. Thus, as illustrated in FIG. 3A the first fluid F1 is moved toward the center of the aperture adjuster 101 via the first channel C1 so that the narrowed aperture A1 may be obtained. When a suitable voltage is applied to the second electrode unit 180, the first fluid F1 is moved toward the center of the aperture adjuster 101 via the second channel C2. Accordingly, as illustrated in FIG. 3B, the TCL of the first channel C1 is moved toward the periphery of the aperture adjuster 101, resulting in the widened aperture A2. When the first electrode unit 120 includes a plurality of electrodes E, the size of the aperture of the aperture adjuster 101 may be digitally controlled by changing an activated electrode.

Although the size of the aperture is A1 in an OCT mode in FIG. 3A, and the size of the aperture is A2 in an OCM mode in FIG. 3B, the sizes are only examples. The sizes of the apertures A1 and A2 may vary according to design conditions.

Referring back to FIG. 2, the aperture adjuster 50 may include a cover glass 51 on at least one of an input end and an output end of the aperture adjuster 50. FIG. 2 illustrates a case where the aperture adjuster 50 includes the cover glass 51 on the input end thereof. In FIG. 2, reference numeral 55 denotes a portion of the aperture adjuster 50 in which aperture adjustment is performed.

When a fluid flows according to the electrowetting principle, and the size-adjusted apertures A1 and A2 are obtained in FIGS. 3A and 3B, the first substrate 110 or the third substrate 190 of the aperture adjuster 101 may be used as a cover glass. However, a separate cover glass may be further included.

Referring to FIGS. 2, 3A, and 3B, the filter unit 40 includes a center region 41, which transmits incident light without changing the incident light, and a filter region 45, which surrounds the center region 41 and increases the DOF of light which is focused on an ultra-close location.

The center region 41 may be an opening or a transparent flat plate. As seen from a comparison between FIGS. 3A and 3B, the center region 41 may have a size equal to or greater than the size of an incident light beam which has been diminished into a relatively small size by the aperture adjuster 101 in a close mode, e.g., an OCT mode. At this time, the center region 41 may be formed to have a radius about 0.2 to about 0.5 times as large as the radius of the aperture A2 of the aperture adjusters 101 and 102 in an ultra-close mode, e.g., an OCM mode, and a minimum diameter of the center region 41 may include the diameter of the aperture A1 of the aperture adjusters 101 and 102 in a close mode, e.g., an OCT mode. FIG. 3A illustrates a case where the center region 41 is formed to have a size corresponding to the aperture A1 in an OCT mode.

The filter region 45 is a phase filter and may be formed in the structure of a ring that surrounds the center region 41. In this case, a minimum radius of the filter region 45 may be equal to or greater than the radius of the aperture A1 of the aperture adjusters 101 and 102 in a close mode, e.g., in an OCM mode.

The filter region 45 may be implemented using a cubic filter that satisfies the equation of $\theta(x, y)=\alpha(x^\beta+y^\beta)$, where the value of $\alpha$ may be about 0.0001 to about 0.02, and the value of $\beta$ may be about 2.6 to about 3.1.

The filter region 45 may be implemented using a cubic-petal filter that satisfies the equation of $\theta(x, y)=\alpha(x^3+y^3)+\beta(x^2y+xy^2)$, where the value of $\alpha$ may be about $-0.005$ to about $+0.005$, and the value of $\beta$ may be about $-0.015$ to about $+0.015$.

The above-described filter unit 40 may be included in the aperture adjuster 50, or may be formed as a phase filter and disposed on the traveling path of parallel light beams before and after the aperture adjuster 101.

In other words, as illustrated in FIGS. 2 through 11, the filter unit 40 may be included in the aperture adjusters 50, 101, and 102.

Instead of being included in the aperture adjuster 50, the filter unit 40 may be formed as a phase filter on the traveling path of parallel light beams, before and after the aperture adjuster 50. As described above, in the optical zoom probe 10, light incident upon the aperture adjuster 50 from the first lens unit 30 is parallel light or substantially parallel light. As seen from FIGS. 9A through 10, which will be described later, light having passed through the aperture adjuster 50 travels in the form of parallel light until a certain place.

The optical zoom probe 10 may use the aperture adjuster 102 of FIG. 4 as the aperture adjuster 50, instead of using the aperture adjuster 101 of FIGS. 3A and 3B.

FIG. 4 illustrates the aperture adjuster 102, which may be employed in the optical zoom probe 10 of FIG. 2.

The aperture adjuster 102 of FIG. 4 is different from the aperture adjusters 101 of FIGS. 3A and 3B in that a third electrode unit 320 and a fourth electrode unit 380, each including at least one electrode E coated with an insulation material I, are further included on both surfaces of the second substrate 150, respectively. The third electrode unit 320 may increase a driving force generated in the first channel C1, in cooperation with the first electrode unit 120, and the fourth electrode unit 380 may increase a driving force generated in the second channel C2, in cooperation with the second electrode unit 180. The number of electrodes E included in each of the third and fourth electrode units 320 and 380 may vary, and is not limited to the number of electrodes illustrated in FIG. 4. In FIG. 4, although the third electrode unit 320 and the fourth electrode unit 380 are provided on both surfaces of the second substrate 150, respectively, this is only an example. The third electrode unit 320 or the fourth electrode unit 380 may be provided on only one surface of the second substrate 150.

Referring back to FIG. 2, the second lens unit 60 is provided to transmit light having passed through the aperture adjuster 50 to the focus adjustment unit 70, and may include at least one lens.

The focus adjustment unit 70 may include first and second liquid lenses 71 and 75, of which curvatures are independently controlled to focus the light transmitted by the aperture of the aperture adjuster 50, and to adjust a focal length.

A transparent medium 73 may be interposed between the first liquid lens 71 and the second liquid lens 75, and the first liquid lens 71 and the second liquid lens 75 may be integrally formed with the transparent medium 73 interposed therebetween. In this case, to optimize the focus adjustment unit 70 in a lengthwise direction, the first and second liquid lenses 71 and 75 may be arranged to have only one transparent medium 73 interposed therebetween, and to move in opposite directions during focus adjustment. During adjustment of the curvatures of the first and second liquid lenses 71 and 75, the focus adjustment unit 70 may be driven so that the protrusion variations of the first and second liquid lenses 71 and 75 do not exceed about 400 μm.

Each of the first and second liquid lenses 71 and 75 may form a lens surface using the surface of a fluid, and may adjust the shape of the lens surface using the flow of the fluid to thereby adjust a focal length.

Figure 9A:
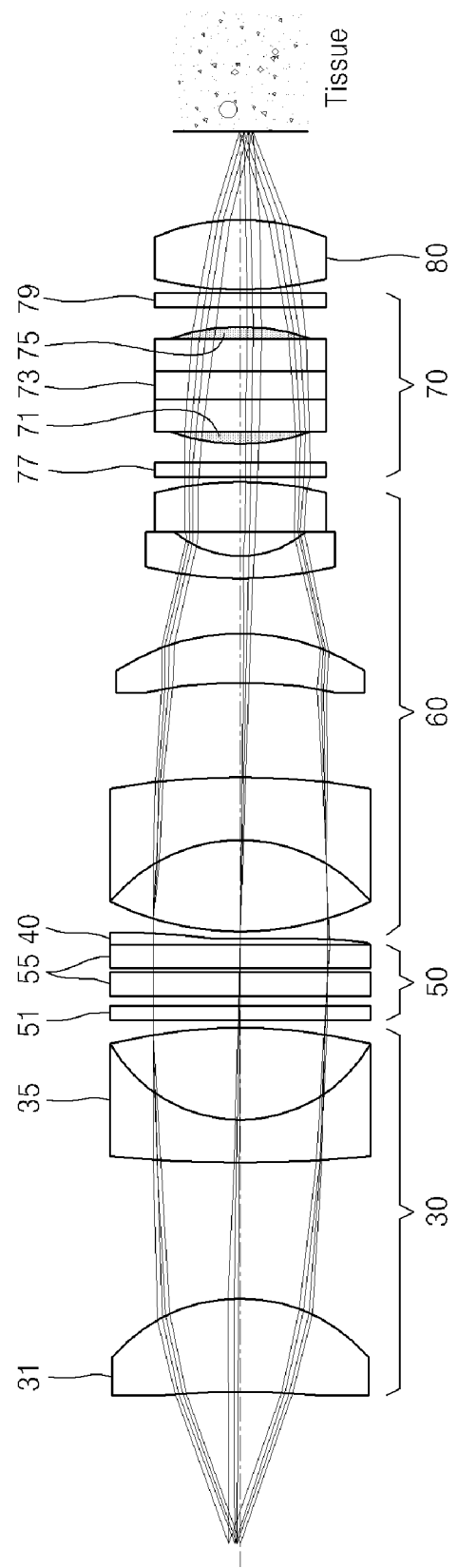
FIGS. 9A and 9B illustrate operations of the optical zoom probe of FIG. 2 when scanning is performed in the range of the surface of a target, for example, tissue, to a relatively shallow depth from the surface of the tissue.
Figure 9B:
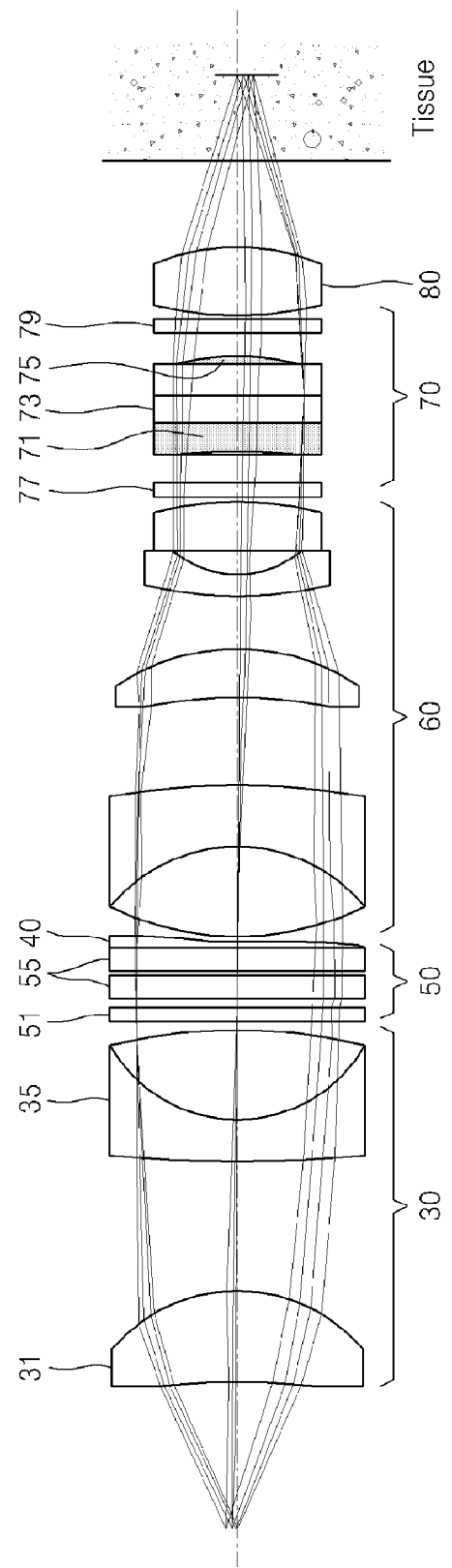

When the optical zoom probe 10 performs x-y scanning in a certain range, e.g., from about 2 mm to about 4 mm, in the depth direction of the tissue from an ultra-close location where a distance between the last lens (i.e., the lens 80 of FIG. 2) of the optical zoom probe 10 and a target, e.g., tissue, is an ultra-close distance, e.g., about 2 mm or less, e.g., in an OCM mode, the first and second liquid lenses 71 and 75 may be driven so that at least one of them has a convex lens surface, as illustrated in FIGS. 9A and 9B. For example, during ultra-close scanning, e.g., in an OCM mode, a liquid lens which is closer to the tissue among the first and second liquid lenses 71 and 75, e.g., the second liquid lens 75, may be driven to have a convex lens surface.

Figure 10:
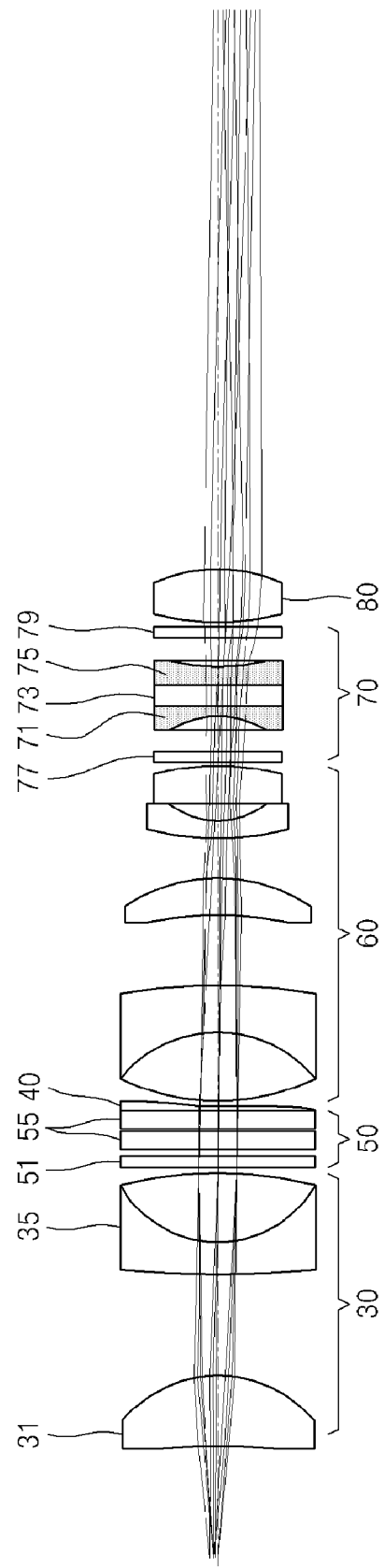
FIG. 10 illustrates an operation of the optical zoom probe of FIG. 2 when scanning is performed in a long focal length.

When the optical zoom probe 10 performs x-y scanning within a certain range in the depth direction of the tissue from a close location where the distance between the last lens (i.e., the lens 80 of FIG. 2) of the optical zoom probe 10 and the target, e.g., tissue, is a close distance, e.g., about 30 mm or less, e.g., in an OCT mode, the first and second liquid lenses 71 and 75 may be driven to have concave lens surfaces, respectively, as illustrated in FIG. 10.

The first and second liquid lenses 71 and 75 may be provided so that a fluid flow occurs according to an electrowetting method.

Figure 5:
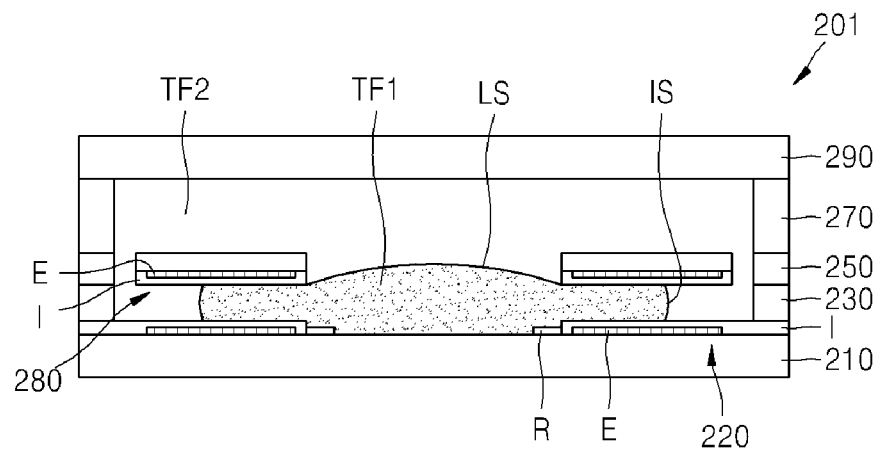
FIG. 5 illustrates an example of a liquid lens that is employable as a first liquid lens or a second liquid lens of a focus adjustment unit of the optical zoom probe of FIG. 2.

FIG. 5 illustrates a liquid lens 201, which may be used as the first liquid lens 71 or the second liquid lens 75 of the focus adjustment unit 70 in the optical zoom probe 10 of FIG. 2.

Referring to FIG. 5, a first fluid TF1, which is transparent and polar, and a second fluid TF2, which is not mixed with the first fluid TF1 and is transparent, are accommodated in the internal space of a chamber of the liquid lens 201. An interface between the first fluid TF1 and the second fluid TF2 includes a first surface LS, which forms a lens surface, and a second surface IS, which induces a curvature change in the lens surface. An electrode unit for forming an electric field which changes the location of the second surface IS is formed within the chamber. The interface between the first fluid TF1 and the second fluid TF2 includes the first surface LS and the second side IS, a first intermediate plate 250 including a first through hole TH3, which forms the diameter of a lens corresponding to the lens surface, and a second through hole TH4, which forms a passage for the second fluid TF2, are provided within the chamber.

A lower substrate 210 and an upper substrate 290 may be provided below and above the first intermediate plate 250, respectively, and spacers may be disposed between the lower substrate 210 and the first intermediate plate 250 and between the first intermediate plate 250 and the upper substrate 290 in order to form internal spaces. The spacers may be a first spacer 230 between the lower substrate 210 and the first intermediate plate 250, and a second spacer 270 between the first intermediate plate 250 and the upper substrate 290.

The lower substrate 210, the first intermediate plate 250, and the upper substrate 290 may be formed of a transparent material.

The first fluid TF1 and the second fluid TF2 may be transparent fluids having different refractive indices. In this case, the first fluid TF1 may be formed of a polar liquid, and the second fluid TF2 may be formed of a vapor or a non-polar liquid.

As illustrated in FIG. 5, the electrode unit may include a first electrode unit 220, which is formed on an upper surface of the lower substrate 210 and includes an electrode E coated with an insulation material I, and a second electrode unit 280, which is formed on a lower surface of the first intermediate plate 250 and includes an electrode E coated with an insulation material I. Only one of the first and second electrode units 220 and 280 may be included.

A ground electrode R, which contacts the first fluid TF1, may be further included. Although the ground electrode R is disposed on the lower substrate 210 in FIG. 5, the ground electrode R may be disposed on any location as long as it may contact the first fluid TF1 when no voltages are applied. The ground electrode R may be optional. When the ground electrode R is included, a reduced driving voltage may be used.

The electrodes E of the first and second electrode units 220 and 280 may be formed of a transparent conductive material. For example, the electrodes E may be formed of a metal oxide such as an ITO or an IZO, a metal nanoparticle dispersion thin film such as Au or Ag, a carbon nanostructure such as CNT or graphene, or a conductive polymer such as PEDOT, PPy, or P3HT. The ground electrode R may be formed of any of the aforementioned transparent conductive materials. When the ground electrode R does not need to be transparent because of its location, it may be formed of a metal thin film, such as Au, Ag, Al, Cr, or Ti.

In the liquid lens 201, a pressure exerted on the second surface IS varies according to electrowetting driving. Accordingly, the curvature of the first surface LS, which is the lens surface, is adjusted. When no voltages are applied or the magnitude of an applied voltage is reduced, the second surface IS may move toward the center. Thus, the first surface LS, which is the lens surface, may become more convex. When the magnitude of the applied voltage is increased, the second surface IS may move toward the periphery, and the curvature of the first surface LS may be decreased. When the applied voltage is maximized, the first surface LS may have a concave curvature.

FIG. 5 illustrates a case where each of the first electrode unit 220 and the second electrode unit 280 includes a single electrode E, and the magnitude of a voltage applied to the electrode E is adjusted to change the location of the second surface IS.

The first electrode unit 220 and the second electrode unit 280 may each include a plurality of electrodes E, each coated with an insulation material I. In this case, the curvature of the first surface LS, which is the lens surface, may be digitally controlled by selecting some of the electrodes E of each of the first and second electrode units 220 and 280, and applying a voltage to the selected electrodes E. In other words, when a suitable voltage is applied to one of the electrodes E of each of the first and second electrode units 220 and 280, an electromechanical force is exerted on a TCL, e.g., a three phase contact line where the second surface IS, which is the interface between the first and second fluids TF1 and TF2, and the insulation material I meet, on the actuated electrode E. Thus, the location of the second surface IS is determined, thereby determining the curvature of the first surface LS. When a suitable voltage is applied to an innermost electrode E from among the electrodes E, the second surface IS is moved toward the center as much as possible. Thus, the curvature of the first surface LS may be increased. When a suitable voltage is applied to an outermost electrode E from among the electrodes, the second surface IS is moved toward the periphery as much as possible. Thus, the curvature of the first surface LS may be decreased or a concave curvature may be formed.

Figure 6:
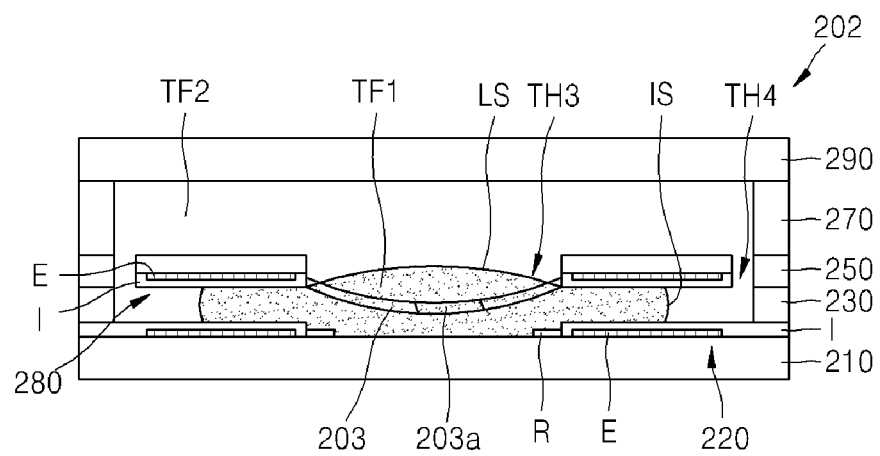
FIG. 6 illustrates another example of a liquid lens that is employable as the first liquid lens or the second liquid lens of the focus adjustment unit of the optical zoom probe of FIG. 2.

FIG. 6 illustrates another example of a liquid lens 202, which may be used as the first liquid lens 71 or the second liquid lens 75 of the focus adjustment unit 70 in the optical zoom probe 10 of FIG. 2.

Referring to FIG. 6, in the liquid lens 202, in the case that shape control of a lens surface of the liquid lens 202 in the z-axis direction is unnecessary or necessary shape deformation of the lens surface is at a minimum due to a long focal distance of about 30 mm, the lens surface may be formed between liquids so as to form a lens shape using a transparent film 203. The liquid lens 202 of FIG. 6 is different from the liquid lens 201 of FIG. 5 in that the liquid lens 202 further includes the transparent film 203. The transparent film 203 may be formed to be concave.

In this case, e.g., in a close mode, the first fluid TF1 and the second fluid TF2 may move so that the first surface LS corresponds to the curved surface of the transparent film 203. Thus, the curved surface of the transparent film 203 may serve as a concave lens surface. In an ultra-close mode, the first surface LS is located above the transparent film 203. Thus, the curved surface of the transparent film 203 may not serve as the lens surface. The transparent film 203 may include a through hole 203a such that the first fluid TF1 or the second fluid TF2 may move therein. FIG. 6 illustrates a case where, since the first fluid TF1 also exists on the transparent film 203, a convex interface between the first fluid TF1 and the second fluid TF2 serves as the lens surface. When the fluid TF1 existing on the transparent film 203 entirely flows out from under the transparent film 203, the concave surface of the transparent film 203 serves as a concave lens surface.

Even in this case, in the liquid lens 202, a pressure exerted on the second surface IS varies by electrowetting driving. Accordingly, the curvature of the first surface LS, which is the lens surface, may be controlled.

In FIGS. 5 and 6, each of the first electrode unit 220 and the second electrode unit 280 includes a single electrode E, and the magnitude of a voltage applied to the electrode E is adjusted to change the location of the second surface IS. However, the first electrode unit 220 and the second electrode unit 280 may each include a plurality of electrodes E. Each of the plurality of electrodes E is coated with an insulation material I. In this case, the curvature of the first surface LS, which is the lens surface, may be digitally controlled by selecting some of the electrodes E of each of the first and second electrode units 220 and 280, and applying a voltage to the selected electrodes E.

Figure 7:
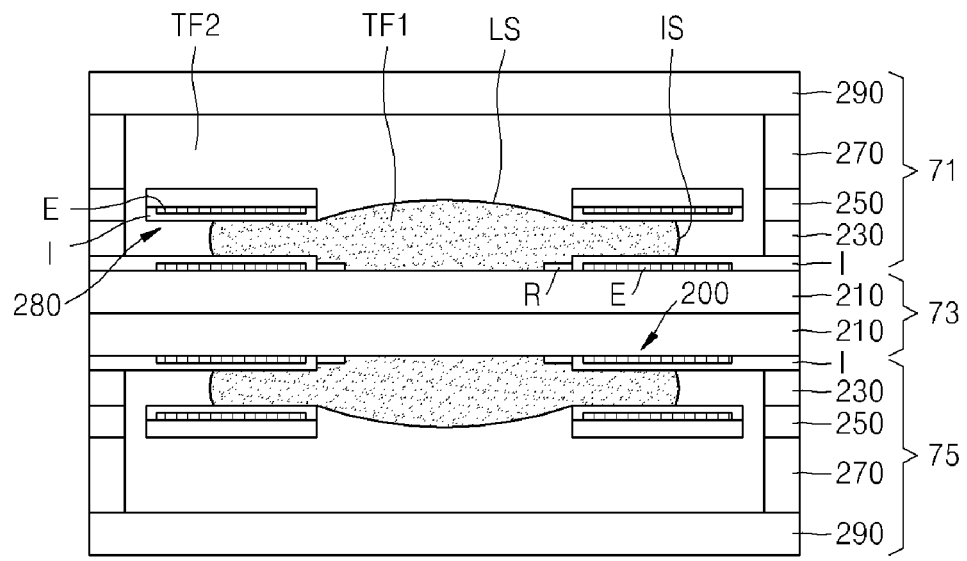
FIG. 7 illustrates a focus adjustment unit including a first liquid lens and a second liquid lens, the focus adjustment unit obtained by symmetrically arranging and coupling the liquid lenses of FIG. 5 to each other.

FIG. 7 illustrates an example where the focus adjustment unit 70 including the first and second liquid lenses 71 and 75 is obtained by symmetrically arranging and coupling two liquid lenses 201 of FIG. 5 to each other. The focus adjustment unit 70 including the first and second liquid lenses 71 and 75 may also be formed by symmetrically arranging and coupling two liquid lenses 202 of FIG. 6 to each other. The first liquid lens 71 and the second liquid lens 75 may be independently controlled to adjust the curvatures thereof.

A transparent medium 73 interposed between the first liquid lens 71 and the second liquid lens 75 may correspond to the lower substrate 210. Alternatively, a separate transparent medium may be further interposed between the first liquid lens 71 and the second liquid lens 75, to serve as the transparent medium 73. In FIG. 7, two lower substrates 210 are coupled to each other by coupling a pair of liquid lenses to each other. However, the focus adjustment unit 70 may include only one lower substrate 210 between the first liquid lens 71 and the second liquid lens 75.

Referring back to FIG. 2, the focus adjustment unit 70 may include cover glasses 77 and 79 on at least one of an input end, and an output end of the focus adjustment unit 70. In FIG. 2, the cover glasses 77 and 79 are provided on an input end and an output end, respectively, of the focus adjustment unit 70.

As illustrated in FIG. 7, when the focus adjustment unit 70 including the first and second liquid lenses 71 and 75 is formed by symmetrically arranging and coupling two liquid lenses to each other, the upper substrates 290 located in upper and lower portions of the focus adjustment unit 70 may be used as cover glasses, or separate cover glasses may be further included in the focus adjustment unit 70.

A case where the first and second liquid lenses 71 and 75 of the focus adjustment unit 70 are provided so that fluid flow occurs according to an electrowetting method has been described above. However, exemplary embodiments are not limited. At least one of the first and second liquid lenses 71 and 75 may be a liquid lens 205 (see FIG. 8), which enables fluid flow to occur according to a pressure type method.

Figure 8:
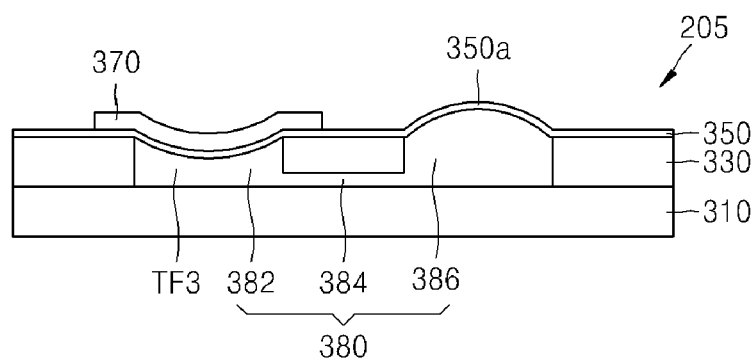
FIG. 8 illustrates another example of a liquid lens that is employable as the first liquid lens or the second liquid lens in the focus adjustment unit of the optical zoom probe of FIG. 2.

FIG. 8 illustrates the liquid lens 205, which may be used as the first liquid lens 71 or the second liquid lens 75 of the focus adjustment unit 70 in the optical zoom probe 10 of FIG. 2.

Referring to FIG. 8, the liquid lens 205 is constructed so that a fluid flow for a change in the curvature of a lens surface occurs according to a pressure type method. The liquid lens 205 includes a transparent fluid TF3 contained in an internal space 380 of a chamber of the liquid lens 205. The internal space 380 of the chamber may be defined by a substrate 310 and a frame 330, formed on the substrate 310, and may include a flow chamber 382, a flow path 384, and a lens chamber 386. A membrane 350 may be disposed above the frame 330, and an actuator 370 may be disposed on a part of the membrane 350 which faces the flow chamber 382. One surface of the membrane 350 that faces the lens chamber 386 may be a lens surface 350a.

The membrane 350 may be formed of a transparent elastic material, e.g., a silicon elastomer. The membrane 350 may also be formed of polydimethylsiloxane (PDMS), which is excellent in durability and flexibility.

The actuator 370 is provided to apply a pressure to the transparent fluid TF3. Various types of commonly-used actuators may be used as the actuator 370. For example, a general polymer actuator formed of an electro active polymer (EAP), which is very thin and consumes small power, may be used, or a relaxor ferroelectric polymer actuator formed of a copolymer, such as P(VDF-TrFE-CFE) or P(VDF-TrFE-CTFE) may be used. Since electrostrictive strain is caused by a voltage application, the actuator 370 may apply a pressure to the transparent fluid TF3, which is adjacent to the actuator 370.

For example, silicon oil may be used as the transparent fluid TF3.

When a pressure is applied to the transparent fluid TF3 within the fluid chamber 382 as the actuator 370 is driven, the transparent fluid TF3 is moved to the lens chamber 386 via the fluid path 384 to thereby change the shape of the lens surface 350a.

Structures other than the aforementioned liquid lenses may be used as the first or second liquid lens 71 or 75 of the focus adjustment unit 70 in the optical zoom probe 10 of FIG. 2. For example, the first liquid lens 71 or the second liquid lens 75 may be a liquid crystal lens which forms an electric field gradient in liquid crystal, and induces a refractive index gradient according to the electric field gradient to adjust a focal length.

In the optical zoom probe 10, the focal length may vary as the curvatures of the first and second liquid lenses 71 and 75 are adjusted, and a resolution may be adjusted as the size of the aperture is adjusted. Moreover, the DOF may be increased by the filter region 45 of the filter unit 40 in an OCM mode.

FIGS. 9A, 9B, and 10 illustrate a depth scanning method performed by the optical zoom probe 10 of FIG. 2. Referring to FIGS. 9A, 9B, and 10, the optical zoom probe 10 of FIG. 2 is capable of scanning a target, while maintaining a horizontal resolution, even when varying a depth within the target.

FIGS. 9A and 9B illustrate operations of the optical zoom probe 10 of FIG. 2 when the target, e.g., tissue, is scanned to a relatively shallow depth from the surface of the tissue by shortening the focal length. FIG. 10 illustrates an operation of the optical zoom probe 10 of FIG. 2 when scanning is performed by lengthening the focal length.

As illustrated in FIG. 9A, when the aperture of the aperture adjuster 50 is set to have an appropriate size and the lens surfaces of the first and second liquid lenses 71 and 75 are made convex, light is focused on the surface of the target, e.g., tissue, at an approximately ultra-close distance, and the filter region 45 of the filter unit 40 may increase the DOF of the light focused at the approximately ultra-close distance by at least several times or more, in comparison with a case where the filter unit 40 is not used. In this case, a distance between the last lens 80 of the optical zoom probe 10 and the tissue may be, e.g., about 2 mm or less. In this case, when the light transmission unit 20 changes a light path by inducing a deformation of the optical fiber 21 using the scanner 23, the surface of the tissue may be scanned within a certain range on an x-y plane.

As illustrated in FIG. 9B, when the aperture of the aperture adjuster 50 is set to have a large size compared with FIG. 9A, the lens surface of the first liquid lens 71 is made slightly concave, and the lens surface of the second liquid lens 75, which is closer to the tissue than the first liquid lens 71, is made convex. A light spot may be focused on a certain depth from the surface of the tissue while maintaining the horizontal resolution of the light spot. For example, the light spot may be focused on a depth of about 2 mm from the surface of the tissue. In this case, when the light transmission unit 20 changes a light path by inducing a deformation of the optical fiber 21 by means of the scanner 23, while forming the light spot at a certain depth, the inside of the tissue may be scanned within a certain range on an x-y plane at the certain depth.

The sizes of the aperture of the aperture adjuster 50 of FIGS. 9A and 9B may be within a certain range of the size of the aperture A2 of FIG. 3B.

In such an OCM mode, a scan in the z-axis direction may be performed in the range of about 2 mm to about 4 mm. For example, the DOF in the z-axis direction in an OCM mode may be made short, e.g., about 10 µm, when the filter unit 40 is not included, whereas the DOF may be made long, namely, about 50 µm, when the filter unit 40 is included as in the optical zoom probe 10 of FIG. 2. Accordingly, in the optical zoom probe 10 of FIG. 2 in an OCM mode, the location of a focal point does not need to be precisely moved because the DOF is long. Thus, ultra-close scanning may be easily and accurately performed. The DOF of about 50 µm, obtained by the optical zoom probe 10 in an OCM mode is illustrated by an example, and exemplary embodiments are not limited. The DOF may vary according to design conditions.

According to such an operation of the optical zoom probe 10 of FIG. 2, an OCM operation corresponding to high-resolution ultra-close (i.e., the case where the distance from the last lens to the surface of tissue is about 2 mm or less) scanning may be performed. In other words, the optical zoom probe 10 of FIG. 2 may optically scan the tissue with a uniform 3-dimensional (3D) spatial resolution within a section of about 2 mm in the depth direction of the tissue from the ultra-close location of about 2 mm or less. At this time, the DOF may be lengthened by the filter region 45. Thus, there is no need to precisely move the location of a focal point. Thus, ultra-close scanning may be more easily and accurately performed.

As illustrated in FIG. 10, when the aperture of the aperture adjuster 50 is set to have a small size compared with FIGS. 9A and 9B (e.g., the size of the aperture A1 of FIG. 3A) and the lens surfaces of the first and second liquid lenses 71 and 75 are made to be concave, a light spot may be focused on a relatively far distance from the last lens, e.g., on an about 30 mm range. In this case, the location on which the light spot is focused may vary depending on adjustment of the size of the aperture of the aperture adjuster 50 and adjustment of the curvatures of the concave surfaces of the first and second liquid lenses 71 and 75. In this case, when the light transmission unit 20 changes a light path by inducing a deformation of the optical fiber 21 using the scanner 23, scanning may be performed within a certain range on an x-y plane, while changing the horizontal location on which the light spot is focused.

As illustrated in FIG. 10, according to an operation of the optical zoom probe 10 of FIG. 2, an OCT operation corresponding to close (i.e., the case where the distance between the last lens to the surface of tissue is about 30 mm or less) scanning may be performed. In other words, the optical zoom probe 10 of FIG. 2 may optically scan the tissue with a uniform 3-dimensional (3D) spatial resolution within a section of about 2 mm in the depth direction of the tissue from the close location of about 30 mm or less.

Thus, when the focal length of the focus adjustment unit 70 is adjusted by adjusting both the aperture size of the aperture adjuster 50 and the curvature directions and curvatures of the lens surfaces of the first and second liquid lenses 71 and 75, the tissue may be optically scanned up to a certain depth, while maintaining a high horizontal resolution.

Although at least the second liquid lens 75, closer to the target from among the first and second liquid lenses 71 and 75, forms a convex surface during ultra-close scanning and both the first and second liquid lenses 71 and 75 form concave surfaces during close scanning in FIGS. 9A, 9B, and 10, exemplary embodiments are not limited. Thus, and various modifications and other equivalent embodiments may be made.

In the optical zoom probe 10 of FIG. 2, components having perpendicular surfaces on a light path may be non-reflectively coated, or have certain inclinations in order to remove noise generated due to reflected light.

Figure 11:
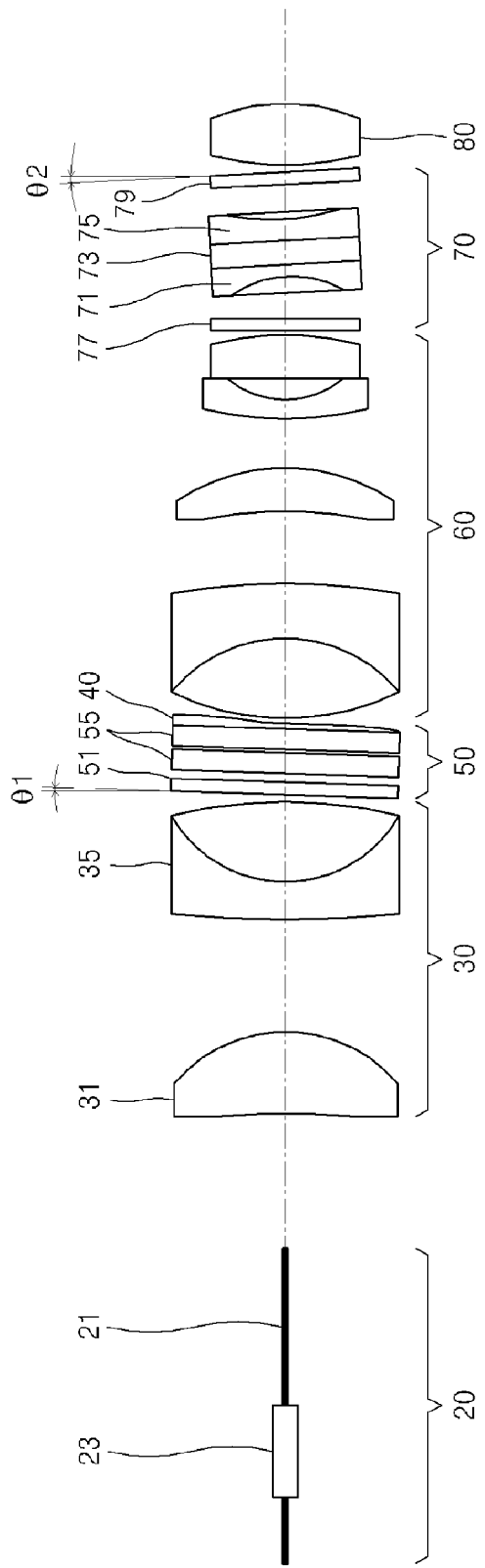
FIG. 11 is a schematic view of an overall optical structure of an optical zoom probe according to another embodiment.

For example, as illustrated in FIG. 11, the cover glass 51 of the aperture adjuster 50 or the cover glasses 77 and 79 of the focus adjustment unit 70 may be arranged in a slant by angles θ1 and θ2 with respect to an optical axis. FIG. 11 illustrates an example in which both the aperture adjuster 50 and the focus adjustment unit 70 are disposed in a slant. However, only one of the aperture adjuster 50 and the focus adjustment unit 70 may be disposed in a slant.

The inclination angle may be 12 degrees or less. In other words, the cover glass 51 of the aperture adjuster 50, or the cover glasses 77 and 79 of the focus adjustment unit 70 may be arranged to have an inclination of about 12 degrees or less, e.g., about 4 to about 12 degrees, with respect to the optical axis. For example, the cover glass 51 of the aperture adjuster 50 or the cover glasses 77 and 79 of the focus adjustment unit 70 may be arranged to have an inclination of about 8 degrees with respect to the optical axis.

Figure 12:
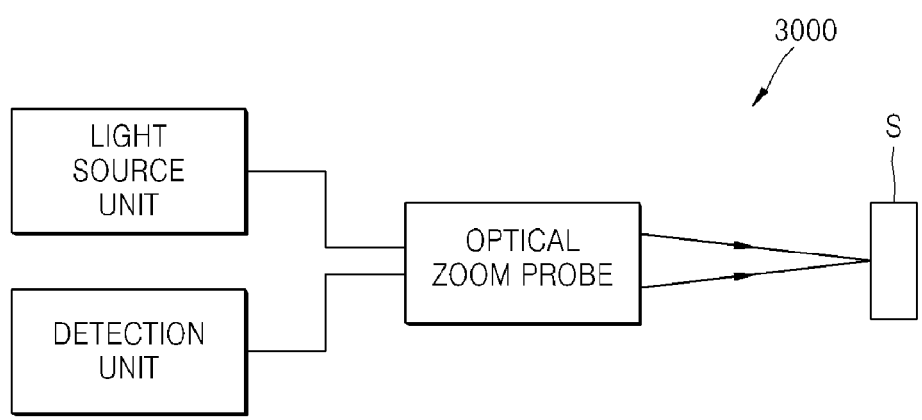
FIG. 12 is a block diagram of an image diagnosis system that uses an optical zoom probe according to an embodiment.

FIG. 12 is a block diagram of an image diagnosis system 3000 using an optical zoom probe according to an embodiment.

Referring to FIG. 12, the image diagnosis system 3000 includes a light source unit, the optical zoom probe, which scans a target S, e.g., a tissue to be inspected, using the light output from the light source unit, and a detection unit which detects an image of the target S from light reflected by the target S.

The optical zoom probe may be the optical zoom probe 10 according to an exemplary embodiment as described above, and the aperture size, focal length, etc., may be suitably adjusted according to inspection purposes. The detection unit may include an image sensor such as a charge-coupled device (CCD) for sensing an image of a target.

The image diagnosis system 3000 may further include a beam separator which separates the path of light radiated by the light source unit toward the target S from the path of light reflected by the target S, and an image signal processing unit which processes a signal detected by the detection unit into an image signal and displays the image signal.

The image diagnosis system 3000 may be configured to scan the to-be-inspected tissue using the optical zoom probe 10 and allow the light reflected by the to-be-inspected tissue to interfere with reference light to detect signal light. To this end, the optical zoom probe 10 may further include an optical system which splits into two light beams the light emitted from the same light source as a light source of the light radiated onto the target S, e.g., from the light source unit, uses one light beam as the light radiated onto the target S and the other as reference light, and makes the light reflected by the target S interfere with the reference light.

In this case, when the optical zoom probe 10 scans the target S while moving a focal point between an ultra-close distance section and a close distance section, e.g., during mode conversion between an OCM mode and an OCT mode, the length of a light path of the light radiated onto the target S is changed. Accordingly, the length of an optical path of the reference light needs to be changed.

Figure 13:
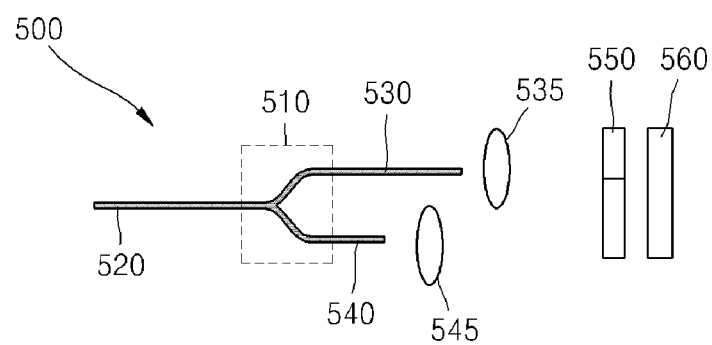
FIGS. 13 through 15 are schematic views of various optical systems that are applicable to adjust the length of a path of reference light, when being used in an optical coherence microscopy (OCM) mode and an optical coherence tomography (OCT) mode.
Figure 14:
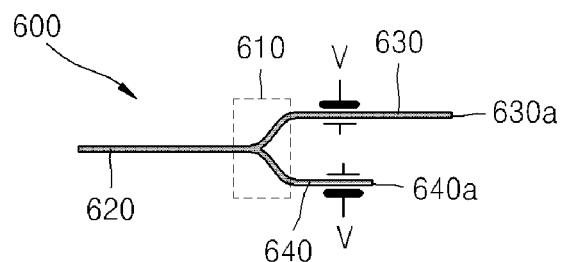
Figure 15:
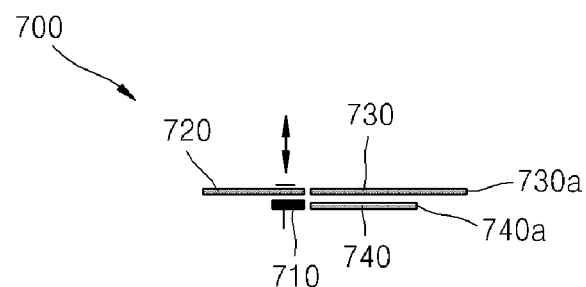

FIGS. 13 through 15 are schematic views of various optical systems 500, 600, and 700, which are applicable to adjust the length of the light path of the reference light, when used in an OCM mode and an OCT mode.

FIGS. 13 and 14 illustrate the optical systems 500 and 600, which progress reference light to different lengths of optical fibers according to modes using couplers 510 and 610, respectively.

Referring to FIG. 13, one end of the coupler 510 is coupled to a single optical fiber 520, and the other end thereof is coupled to two optical fibers 530 and 540, having different lengths from each other. Collimating lenses 535 and 545 may be provided on respective input/output ends of the optical fibers 530 and 540, respectively. The collimating lenses 535 and 545 collimate reference light output by the optical fibers 530 and 540 and focus reference light reflected by a reflection mirror 560 so that the focused reference light is incident upon the optical fibers 530 and 540. A shutter 550 may be disposed between the optical fibers 530 and 540 and the reflection mirror 560.

For example, when a light path of the reference light is desired to be relatively long, the shutter 550 may transmit the reference light output by the optical fiber 530, which is longer, and block the reference light output by the optical fiber 540, which is shorter. The reference light output by the optical fiber 530 and transmitted by the shutter 550 is reflected by the reflection mirror 560, passes through the shutter 550 again, and is incident upon the optical fiber 530.

On the other hand, when a light path of the reference light is desired to be relatively short, the shutter 550 may transmit the reference light output by the optical fiber 540, which is shorter, and block the reference light output by the optical fiber 530, which is longer. The reference light output by the optical fiber 540 and transmitted by the shutter 550 is reflected by the reflection mirror 560, passes through the shutter 550 again, and is incident upon the optical fiber 540.

Referring to FIG. 14, one end of the coupler 610 is coupled to a single optical fiber 620, and the other end thereof is coupled to two optical fibers 630 and 640 having different lengths from each other. Input/output ends 630a and 640a of the optical fibers 630 and 640 may be reflectively coated with a reflective material, such as Au or Ag, so as to reflect reference light output by the optical fibers 630 and 640 without changes and direct the reflected reference light back to the optical fiber 630 and 640. The optical fibers 630 and 640, having different lengths, may be selectively blocked by the action of an external force according to voltage application.

FIG. 15 illustrates the optical system 700, which directs reference light propagating through an optical fiber 720 toward one of optical fibers 730 and 740 having different lengths according to modes using an optical switch 710. Input/output ends 730a and 740a of the optical fibers 730 and 740 may be reflectively coated with a reflective material, such as Au or Ag, so as to reflect reference light output by the optical fibers 730 and 740 without changes and direct the reflected reference light back to the optical fiber 730 and 740.

An optical zoom probe according to an embodiment is capable of performing a high-resolution scan while moving a focal point between an ultra-close distance section and a close distance section. The optical zoom probe is also capable of obtaining a longer DOF in the ultra-close distance section. Therefore, a scan at an ultra-close distance, e.g., in an OCM mode, may have increased distance precision.

According to another exemplary embodiment, the focus adjustment unit 70, the light transmission unit 20, the filter unit 40, the first lens unit 30, the second lens unit 60, the light source unit, and the detection unit may comprise hardware or a hardware module. Further, the detection unit may comprise at least one processor for detecting.

It should be understood that the exemplary embodiments described therein should be considered in a descriptive sense only and not for purposes of limitation. Descriptions of features or aspects within each embodiment should typically be considered as available for other similar features or aspects in other embodiments.

What is claimed is:

1. An optical zoom probe comprising:
an aperture adjuster that comprises a first fluid that blocks light incident on the aperture adjuster, a second fluid that passes light incident on the aperture adjuster, and an aperture in which the second fluid is filled and about which the first fluid is disposed, the aperture adjuster being configured to adjust a size of the aperture by applying an electric field to change a location of a boundary between the first fluid and the second fluid;
a focus adjuster that comprises at least one liquid lens configured to focus the light passed through the aperture and adjust a focal length to have an ultra-close distance and a close distance, the ultra-close distance being 2 mm or less as measured between a target object and a lens of the optical zoom probe that is placed closest to the target object, the close distance being 2 mm to 30 mm as measured between the target object and the closest lens; and
a filter which comprises a center region in which incident light passes without change, and a filter region disposed about the center region and increases a depth of focus (DOF) of light which is focused on a location that has the ultra-close distance,
wherein the aperture adjuster is further configured to increase a size of a light beam incident on the focus adjuster when the focal length has the ultra-close distance, and to decease the size of the light beam when the focal length has the close distance.

2. The optical zoom probe of claim 1, wherein the center region has a size equal to or greater than a size of an incident light beam which has been reduced by the aperture adjuster when the focal length has the close distance.

3. The optical zoom probe of claim 1, wherein a radius of the center region is 0.2 to 0.5 times a radius of the aperture of the aperture adjuster when the focal length has the ultra-close distance, and a minimum diameter of the center region includes a diameter of the aperture of the aperture adjuster when the focal length has the close distance.

4. The optical zoom probe of claim 1, wherein a minimum radius of the filter region is equal to or greater than a radius of the aperture of the aperture adjuster when the focal length has the close distance.

5. The optical zoom probe of claim 1, wherein the filter region is provided in a ring structure.

6. The optical zoom probe of claim 5, wherein the center region is provided in an opening structure or a transparent flat plate structure.

7. The optical zoom probe of claim 1, wherein the filter region is a cubic filter that satisfies an equation of $\theta(x, y) = \alpha(x^\beta + y^\beta)$,
wherein a value of $\alpha$ is in a range between 0.0001 and 0.02, and a value of $\beta$ is in a range between 2.6 and 3.1.

8. The optical zoom probe of claim 1, wherein the filter region is a cubic petal filter that satisfies an equation of $\theta(x, y) = \alpha(x^3 + y^3) + \beta(x^2 y + xy^2)$,
wherein a value of $\alpha$ is in a range between −0.005 and 0.005, and a value of $\beta$ is in a range between −0.015 and 0.015.

9. The optical zoom probe of claim 1, wherein the filter is included in the aperture adjuster or is provided as a phase filter on a traveling path of parallel light beams before and after the aperture adjuster.

10. The optical zoom probe of claim 1, wherein the filter is provided in an aspherical shape or a hybrid type on a last lens surface in which parallel light passed through the aperture adjuster is directed.

11. The optical zoom probe of claim 1, further comprising an aspherical lens between the focus adjuster and the target object,
wherein the aspherical lens has a positive optical power value.

12. The optical zoom probe of claim 1, wherein the least one liquid lens comprises a first liquid lens and a second liquid lens, in which the first liquid lens and the second liquid lens have curvatures which are independently controlled.

13. The optical zoom probe of claim 12, wherein, when the focal length has the close distance, the first liquid lens and the second liquid lens are driven to have concave lens surfaces and, when the focal length has the ultra-close distance, at least one of the first liquid lens and the second liquid lens is driven to have a convex lens surface.

14. The optical zoom probe of claim 13, wherein, when the focal length has the ultra-close distance, one of the first liquid lens and the second liquid lens which is closer to the target object, is driven to have the convex lens surface.

15. The optical zoom probe of claim 12, wherein
at least one of the first liquid lens and the second liquid lens further comprises a transparent film having a curved surface, and
the curved surface of the transparent film is a lens surface when the focal length has the ultra-close distance, and is not the lens surface when the focal length has the ultra-close distance.

16. The optical zoom probe of claim 12, wherein each of the first liquid lens and the second liquid lens forms a lens surface using a surface of a fluid, and the focal length is controlled by adjusting a shape of the lens surface according to a movement of the fluid.

17. The optical zoom probe of claim 1, further comprising:
at least one of a first lens and a second lens, wherein the first lens collimates the incident light and transmits collimated light to the aperture adjuster, and the second lens is disposed between the aperture adjuster and the focus adjuster, wherein the filter is provided in an aspherical shape or a hybrid type on a last lens surface in which parallel light of the second lens is directed.

18. An image diagnosis system comprising:
a light source device;
the optical zoom probe of claim 1 which irradiates light transmitted by the light source device on the target object to be scanned; and
a detector which detects an image of the target object from light reflected by the target object.

19. An optical zoom probe comprising:
an aperture adjuster that comprises first fluid that blocks light incident on the aperture adjuster, second fluid that passes light incident on the aperture adjuster, and an aperture in which the second fluid is filled and about which the first fluid is disposed, the aperture adjuster being configured to adjust a size of the aperture by applying an electric field to change a location of a boundary between the first fluid and the second fluid;
a focus adjuster that comprises at least one liquid lens configured to focus the light passed through the aperture and adjust a focal length; and
a filter configured to increase a depth of focus (DOF) of light which is focused on an ultra-close location of a target object, the ultra-close location is within 2 mm or less apart from a lens of the optical zoom probe that is placed closest to the target object,
wherein at least one of the aperture adjuster and the focus adjuster is disposed in a slant configuration, and
wherein the aperture adjuster is further configured to increase a size of a light beam incident on the focus adjuster when the focal length has the ultra-close distance.

* * * * *